United States Patent
Uno et al.

(10) Patent No.: US 10,422,751 B2
(45) Date of Patent: Sep. 24, 2019

(54) OPTICAL FIBER CORD AND ABNORMALITY DETECTION SYSTEM

(71) Applicant: FUJITSU LIMITED, Kawasaki-shi, Kanagawa (JP)

(72) Inventors: Kazushi Uno, Atsugi (JP); Fumio Takei, Isehara (JP); Takeo Kasajima, Machida (JP)

(73) Assignee: FUJITSU LIMITED, Kawasaki (JP)

(*) Notice: Subject to any disclaimer, the term of this patent is extended or adjusted under 35 U.S.C. 154(b) by 0 days.

(21) Appl. No.: 15/050,891

(22) Filed: Feb. 23, 2016

(65) Prior Publication Data
US 2016/0169807 A1   Jun. 16, 2016

Related U.S. Application Data

(63) Continuation of application No. PCT/JP2013/075663, filed on Sep. 24, 2013.

(51) Int. Cl.
*G01N 21/65* (2006.01)
*G01K 1/14* (2006.01)
(Continued)

(52) U.S. Cl.
CPC .......... *G01N 21/65* (2013.01); *G01D 5/35364* (2013.01); *G01K 1/143* (2013.01);
(Continued)

(58) Field of Classification Search
CPC .... G01N 21/65; G02B 6/4432; G02B 6/4436; G02B 6/4415; G01M 11/33; G01D 5/35364; G01K 1/143; G01K 11/32
See application file for complete search history.

(56) References Cited

U.S. PATENT DOCUMENTS 3,496,717 A * 2/1970 Costello ............... B62D 55/253
  57/229
3,589,121 A * 6/1971 Mulvey ................ B29C 47/128
  156/47
(Continued)

FOREIGN PATENT DOCUMENTS

CN   203433864 U  *  2/2014
JP   S61-208016 A     9/1986
(Continued)

OTHER PUBLICATIONS https://en.wikipedia.org/wiki/Zylon.*
(Continued)

*Primary Examiner* — Mohamed K Amara
(74) *Attorney, Agent, or Firm* — Fujitsu Patent Center

(57) ABSTRACT

An optical fiber cord includes: an optical fiber; and a cover material covering the optical fiber, the cover material being formed by braiding a plurality of yarns. Moreover, an abnormality detection system includes: the optical fiber covered with the cover material formed by braiding the plurality of yarns; a scattered light detector configured to detect scattered light occurring in the optical fiber and output data on intensity distribution in a longitudinal direction of the optical fiber; and a data processor configured to determine the presence or absence of an abnormality based on the data outputted from the scattered light detector.

18 Claims, 15 Drawing Sheets

(51) Int. Cl.
*G01K 11/32* (2006.01)
*G02B 6/44* (2006.01)
*G01D 5/353* (2006.01)
*G01M 11/00* (2006.01)

(52) U.S. Cl.
CPC ............ *G01K 11/32* (2013.01); *G01M 11/33* (2013.01); *G02B 6/4415* (2013.01); *G02B 6/4432* (2013.01); *G02B 6/4436* (2013.01)

(56) References Cited

U.S. PATENT DOCUMENTS

| | | | | |
|---|---|---|---|---|
| 4,070,911 | A * | 1/1978 | Makin | D04C 1/06 116/DIG. 14 |
| 4,304,462 | A * | 12/1981 | Baba | G02B 6/4415 385/107 |
| 4,342,500 | A * | 8/1982 | Oestreich | G02B 6/4415 385/113 |
| 4,441,787 | A * | 4/1984 | Lichtenberger | G02B 6/4402 385/107 |
| 4,645,298 | A * | 2/1987 | Gartside, III | G02B 6/4401 385/103 |
| 4,770,489 | A * | 9/1988 | Saito | G02B 6/4407 385/110 |
| 4,896,940 | A * | 1/1990 | Kathiresan | G02B 6/4403 385/112 |
| 4,963,020 | A | 10/1990 | Luthra et al. | |
| 5,189,721 | A * | 2/1993 | Sayegh | G02B 6/4403 385/114 |
| 5,440,660 | A * | 8/1995 | Dombrowski | G02B 6/4402 385/100 |
| 5,822,485 | A * | 10/1998 | Nelson | G02B 6/4432 385/112 |
| 5,838,860 | A * | 11/1998 | Kingstone | F21S 10/005 385/100 |
| 6,314,856 | B1 * | 11/2001 | Keith | B29D 23/001 87/1 |
| 6,423,262 | B1 * | 7/2002 | Van Wijk | G01N 21/65 264/408 |
| 6,553,167 | B2 * | 4/2003 | Hurley | G02B 6/4432 385/102 |
| 7,848,604 | B2 * | 12/2010 | Reed | G02B 6/4432 385/100 |
| 8,142,501 | B2 * | 3/2012 | Macossay-Torres | A61F 2/08 623/13.2 |
| 8,218,927 | B2 * | 7/2012 | Chang | A61B 5/0062 356/450 |
| 8,335,418 | B2 * | 12/2012 | Hurley | B29D 11/00663 385/102 |
| 8,620,124 | B1 * | 12/2013 | Blazer | G02B 6/4489 385/102 |
| 9,075,212 | B2 * | 7/2015 | McAlpine | G02B 6/4413 |
| 9,146,165 | B2 * | 9/2015 | Hartog | G01L 1/242 |
| 9,362,021 | B2 * | 6/2016 | Winterhalter | H01B 5/105 |
| 9,690,062 | B2 * | 6/2017 | Hurley | G02B 6/4434 |
| 9,733,443 | B2 * | 8/2017 | Blazer | G02B 6/4489 |
| 9,791,652 | B2 * | 10/2017 | Aguilar | G02B 6/4433 |
| 10,025,053 | B2 * | 7/2018 | Hudson, II | G02B 6/4433 |
| 2003/0072545 | A1 * | 4/2003 | Kusakari | G02B 6/4432 385/101 |
| 2008/0061572 | A1 | 3/2008 | Harada et al. | |
| 2008/0253428 | A1 * | 10/2008 | MacDougall | G01K 11/32 374/137 |
| 2009/0046983 | A1 * | 2/2009 | Varkey | G02B 6/443 385/113 |
| 2009/0074367 | A1 * | 3/2009 | Shinoski | G02B 6/4427 385/113 |
| 2011/0135816 | A1 * | 6/2011 | Burns | B29D 11/00663 427/163.2 |
| 2012/0033206 | A1 * | 2/2012 | Uno | G01B 11/03 356/73.1 |
| 2012/0033709 | A1 | 2/2012 | Kasajima et al. | |
| 2012/0053419 | A1 * | 3/2012 | Bloom | A61M 25/0013 600/146 |
| 2012/0082422 | A1 * | 4/2012 | Sarchi | G01K 11/32 385/101 |
| 2012/0099825 | A1 * | 4/2012 | Messer | G02B 6/4432 385/113 |
| 2012/0174683 | A1 * | 7/2012 | Kemnitz | G01L 1/242 73/800 |
| 2013/0242283 | A1 * | 9/2013 | Bailey | G01S 17/89 356/4.01 |
| 2013/0265569 | A1 * | 10/2013 | Le Floch | G01D 5/35364 356/73.1 |
| 2014/0049786 | A1 * | 2/2014 | Knuepfer | G01B 11/02 356/634 |
| 2015/0253526 | A1 * | 9/2015 | Sandate Aguilar | G02B 6/441 385/103 |
| 2016/0238461 | A1 * | 8/2016 | Arioka | G01K 11/32 |
| 2016/0306129 | A1 * | 10/2016 | Hurley | G02B 6/4434 |
| 2017/0007310 | A1 * | 1/2017 | Rajagopalan | A61F 5/0079 |
| 2017/0023347 | A1 * | 1/2017 | Ouellette | D07B 1/145 |
| 2017/0056616 | A1 * | 3/2017 | Leeflang | A61M 25/0113 |

FOREIGN PATENT DOCUMENTS

| | | |
|---|---|---|
| JP | 2-291938 | 12/1990 |
| JP | 06-273644 A | 9/1994 |
| JP | H08-094892 A | 4/1996 |
| JP | 09-018428 A | 1/1997 |
| JP | 2003-232013 A | 8/2003 |
| JP | 2007-248332 A | 9/2007 |
| JP | 2008-515740 | 5/2008 |
| JP | 2009-002676 A | 1/2009 |
| JP | 2009-229311 A | 10/2009 |
| JP | 2013-104700 | 5/2013 |
| WO | 2010125712 A1 | 11/2010 |

OTHER PUBLICATIONS http://www.polymerlibrary.com/OpenAccessPDFs/1089315.pdf.*
"Poly(trimethylene terephthalate)—The New Generation of Engineering Thermoplastic Polyester" to Chan (2012).*
http://www.engineeringtoolbox.com/young-modulus-d_417.html.*
https://en.wikipedia.org/wiki/Single-mode_optical_fiber.*
http://www.arcelect.com/fibercable.htm.*
http://netcomposites.com/guide-tools/guide/resin-systems/.*
Espacenet English Machine translation of CN 203433864 U.*
AIPN English Machine TRanslation of JP 2009-229311.*
https://www.thefreedictionary.com/intersect.*
"Cables: A Chronological Perspective", Bartnkas. Wiley-IEEE press (Year: 2003).*
JPOA—Japanese Office Action dated Oct. 4, 2016 for corresponding to Japanese Patent Application No. 2015-538651, with partial English translation of the Office Action.
International Search Report and Written Opinion of the International Searching Authority (Form PCT/ISA/210, Form PCT/ISA/237), dated Dec. 3, 2013 in connection with PCT/JP2013/075663 (8 pages).
JPOA—Office Action dated May 9, 2017 for corresponding Japanese Patent Application No. 2015-538651, with full machine translation of the Office Action.

* cited by examiner

FIG.5

| | HEAT RESISTANCE TEMPERATURE | YOUNG'S MODULI |
|---|---|---|
| OPTICAL FIBER | 1000°C | 70GPa |
| POLYIMIDE | 300~400°C | 5.8GPa |
| PBO (ZYLON) FIBER | 650°C | 180~270GPa |
| PAN BASED CARBON FIBER | 1000°C OR MORE | 240GPa |
| HIGH-SILICA GLASS FIBER | 500~1000°C | 70GPa |

| No. | MATERIAL OF SIDE YARN | THICKNESS (COUNT) | NUMBER OF SIDE YARNS | BRAIDING PITCH | ELONGATION OF COVER MATERIAL |
|---|---|---|---|---|---|
| 1 | HIGH-SILICA GLASS | 200g/km | 32 | 9.6mm | 1.6mm OR MORE |
| 2 | HIGH-SILICA GLASS | 200g/km | 24 | 7.4mm | 2.0mm OR MORE |
| 3 | HIGH-SILICA GLASS | 200g/km | 24 | 10.7mm | 20mm OR MORE |
| 4 | HIGH-SILICA GLASS | 200g/km | 16 | 9.7mm | 11mm OR MORE |
| 5 | PBO FIBER ZYLON | 1110g/10km | 16 | 9.7mm | 40mm OR MORE |

DISTANCE

LENGTH (m)

OPTICAL FIBER CORD AND ABNORMALITY DETECTION SYSTEM

CROSS-REFERENCE TO RELATED APPLICATION

This application is a continuation of International Patent Application No. PCT/JP2013/075663 filed Sep. 24, 2013 and designated the U.S., the entire contents of which are incorporated herein by reference.

FIELD

The embodiment discussed herein is related to an optical fiber cord and an abnormality detection system.

BACKGROUND

In facilities handling large amounts of flammable materials, explosives, and hazardous materials such as a chemical plant, an oil refinery, and a power plant, it is important to prevent a serious accident by detecting corrosion and thickness reduction of pipes and tanks at an early stage.

To this end, an abnormality detection system including a distributed temperature sensor (DTS) using an optical fiber as a temperature sensor is employed in some cases.

In such an abnormality detection system, the optical fiber is laid around, for example, pipes and tanks, and an end portion of the optical fiber is connected to the distributed temperature sensor. Then, laser light is emitted from the distributed temperature sensor into the optical fiber, and Raman scattered light occurring in the optical fiber is detected by the distributed temperature sensor to obtain the temperatures of the pipes, tanks, and the like. The presence or absence of an abnormality is determined based on the obtained results.

In facilities such as a chemical plant, an oil refinery, and a power plant, delay of abnormality detection may lead to a serious accident. Accordingly, there is a demand for a system which may detect occurrence of an abnormality at an earlier stage.

Note that techniques relating to the present application are disclosed in Japanese Laid-open Patent Publication No. 09-18428, Japanese Laid-open Patent Publication No. 2003-232013, Japanese Laid-open Patent Publication No. 06-273644 and International Publication Pamphlet No. WO 2010/125712.

SUMMARY

One aspect of a disclosed technique provides an optical fiber cord including: an optical fiber; and a cover material covering the optical fiber, the cover material being formed by braiding a plurality of yarns.

Another aspect of a disclosed technique provides an abnormality detection system including: an optical fiber covered with a cover material formed by braiding a plurality of yarns; a scattered light detector configured to detect scattered light occurring in the optical fiber and output data on intensity distribution of the scattered light in a longitudinal direction of the optical fiber; and a data processor configured to determine presence or absence of an abnormality based on the data outputted from the scattered light detector.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 5 is a table depicting the heat resistance temperatures and the Young's moduli of the optical fiber, polyimide, a PBO fiber, a PAN-based carbon fiber, and a high-silica glass fiber;

DESCRIPTION OF EMBODIMENT

Before describing an embodiment, a prelude for facilitating the understanding of the embodiment is described below.

As described above, a system configured to detect an abnormality in facilities such as a chemical plant by using an optical fiber as a temperature sensor has been conventionally proposed. Meanwhile, an abnormality detection system according to the embodiment to be described later detects an abnormality by utilizing changes in transmission loss of an optical fiber due to application of bending stress.

Figure 1:
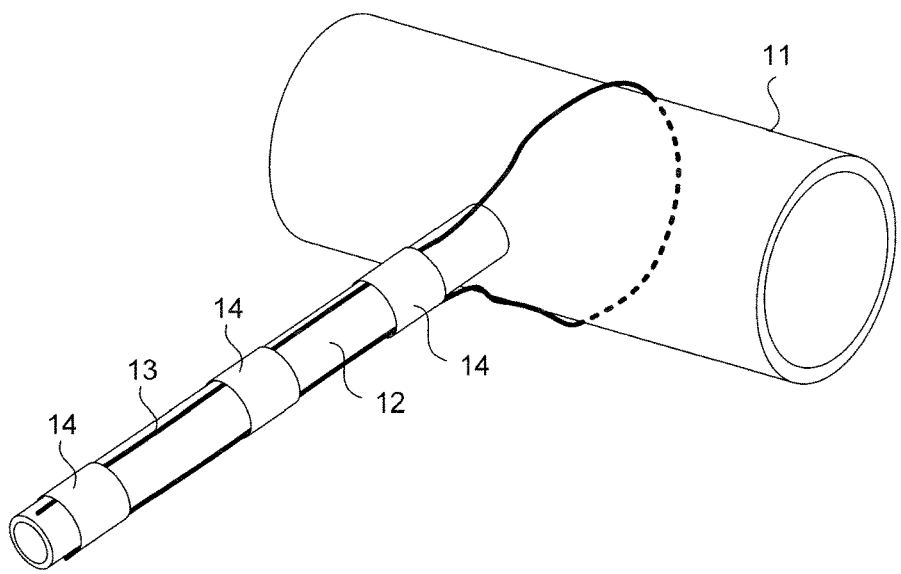
FIG. 1 is a view illustrating a state where an optical fiber is wound at a certain tension around a portion where a branch pipe is welded to a main pipe.

FIG. 1 is a view illustrating a state where an optical fiber 13 is wound at a certain tension around a portion where a branch pipe 12 is welded to a main pipe 11. The optical fiber 13 is partially fixed to the branch pipe 12 by tapes 14.

A flow of solution or gas inside the main pipe 11 and the branch pipe 12 changes with operation and stop of the plant, and the temperature of the main pipe 11 and the branch pipe 12 changes. This temperature change causes the main pipe 11 and the branch pipe 12 to expand or contract, and bending stress and tensile stress applied to the optical fiber 13 thereby changes.

The transmission loss of the optical fiber 13 increases when the bending stress or tensile stress applied to the optical fiber 13 reaches or exceeds a certain degree. Hence, the presence or absence of an abnormality may be determined by, for example, comparing the past transmission loss at the time of operation or stop with the current transmission loss.

Figure 2:
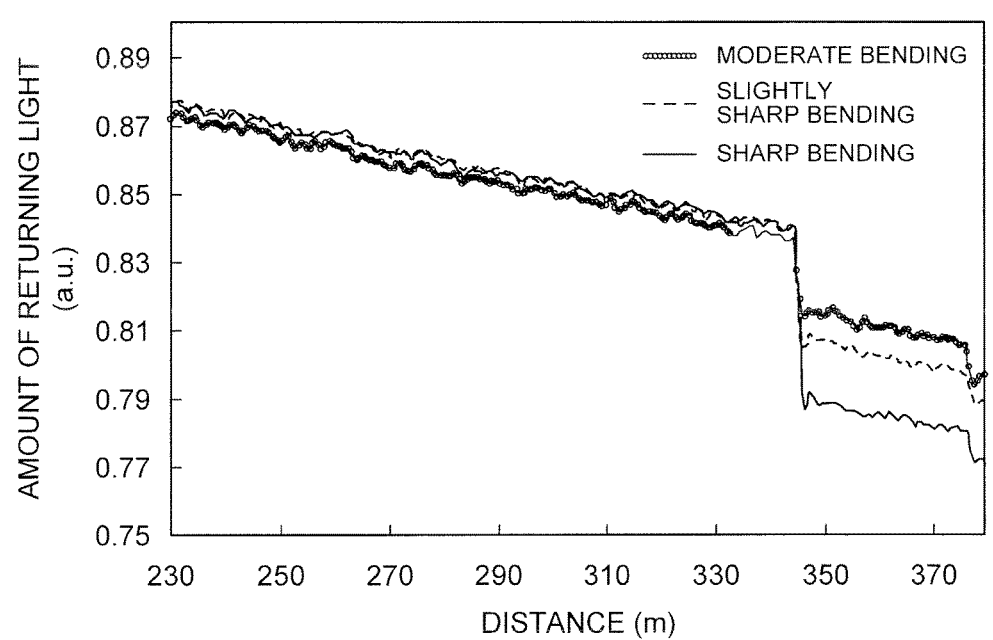
FIG. 2 is a graph depicting results of examining transmission loss in situations where bending of an optical fiber is moderate, slightly sharp, and sharp.

FIG. 2 is a graph depicting results of examining the transmission loss in situations where bending of an optical fiber is moderate, slightly sharp, and sharp, where the horizontal axis represents the distance (position in the longitudinal direction of the optical fiber) and the vertical axis represents the intensity of returning light.

Figure 3A:
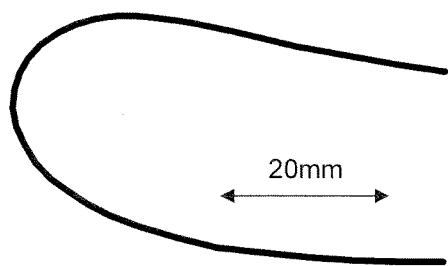
FIGS. 3A to 3C are views specifically illustrating the moderate bending, the slightly sharp bending, and the sharp bending of the optical fiber.
Figure 3B:
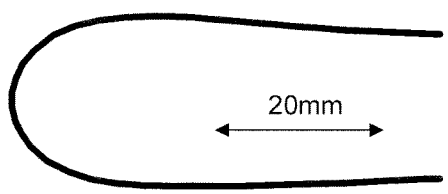
Figure 3C:
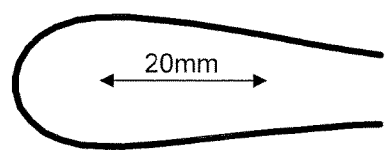

Note that the moderate bending is bending of a level illustrated in FIG. 3A (a bending radius of about 10 mm), the slightly sharp bending is bending at a level slightly shaper than that in FIG. 3A (see FIG. 3B), and the sharp bending is bending at a level slightly shaper than that in FIG. 3B (see FIG. 3C). Moreover, in FIG. 2, the intensity of the returning light is standardized based on the amount light at a position of 0 m in the longitudinal direction of the optical fiber.

It may be seen in FIG. 2 that the transmission loss corresponding to the bending of each level occurs at a position of about 340 m in the longitudinal direction of the optical fiber.

For example, in a normal operation, the optical fiber is moderately bent, and a constant amount of transmission loss is occurring at a certain position in the longitudinal direction of the optical fiber. In this case, when the amount of transmission loss of the optical fiber abruptly changes, the abnormality detection system may determine that some kind of abnormality has occurred.

In facilities such as a chemical plant, portions which need abnormality detection in pipes and the like are generally high-temperature portions. Accordingly, an optical fiber serving as a sensor preferably has resistance against heat of, for example, 300° C. or more to actually detect an abnormality by using the method described above in facilities such as a chemical plant.

A carbon-coated optical fiber and a polyimide-coated optical fiber have heat resistance high enough to be used continuously in an environment of 300° C. or more. However, since the thickness of the coating is small, these optical fibers do not have sufficient mechanical strength. Thus, when the optical fibers are laid along pipes as in FIG. 1, occurrence of abrasion in the optical fibers or, in excessive cases, breakage of the optical fibers is conceivable.

Optical fiber cables with high heat resistance and high mechanical strength include an optical fiber cable in which a carbon-coated or polyimide-coated optical fiber is housed in a stainless steel pipe. However, housing the optical fiber in the stainless steel pipe prevents stress from being transmitted to the optical fiber when the stress is applied to the stainless steel pipe. Accordingly, detection of an abnormality is not possible.

In the following embodiment, description is given of an optical fiber cord which has sufficient responsiveness to stress in addition to sufficient heat resistance and sufficient mechanical strength, and an abnormality detection system using the optical fiber cord.

In the following description, primary-coated optical fiber refers to an object obtained by applying a thin coat of carbon, resin, or the like on an optical fiber made of core and cladding to protect the optical fiber or to improve heat resistance. Moreover, secondary-coated optical fiber refers to an object obtained by adding a secondary coating material to the primary-coated optical fiber to improve strength, water resistance, or the like. Furthermore, optical fiber cord refers to an object obtained by adding a braided cover material to the primary-coated optical fiber or the secondary-coated optical fiber to facilitate handling.

Embodiment

Figure 4A:
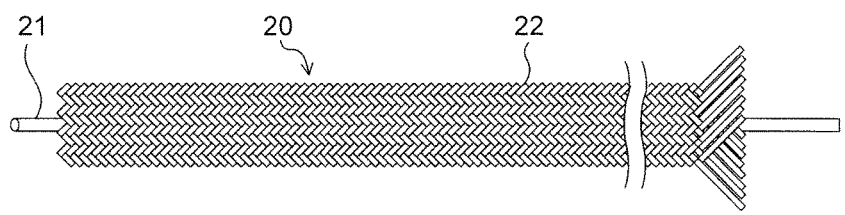
FIG. 4A is a schematic plan view illustrating a structure of an optical fiber cord according to the embodiment.
Figure 4B:
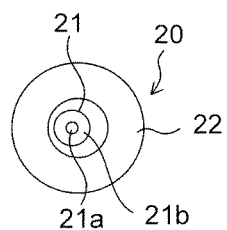
FIG. 4B is a schematic cross-sectional view of the same.

FIG. 4A is a schematic plan view illustrating a structure of an optical fiber cord according to the embodiment, and FIG. 4B is a schematic cross-sectional view of the same.

The optical fiber cord 20 according to the embodiment includes a primary-coated optical fiber 21, and a cover material 22 covering a periphery of the primary-coated optical fiber 21.

The primary-coated optical fiber 21 is obtained by coating a periphery of an optical fiber 21a including a core and a cladding with two layers of a carbon layer and a polyimide layer in this order, the carbon and polyimide being coating materials 21b. The thickness of the carbon layer is, for example, 100 nm or less, and the thickness of the polyimide layer is, for example, 30 μm or less Coating the periphery of the optical fiber 21a with the thin layers of carbon and polyimide as described above improves resistance against bending, and a crack is less likely to be formed in the optical fiber 21a when bending stress is repeatedly applied to the optical fiber 21a.

The cover material 22 is obtained by braiding yarns made of a heat-resistant fiber. A glass fiber (high-silica glass fiber) with a $SiO_2$ component of 60% or more, a PAN (polyacrylonitrile) based carbon fiber, a PBO (poly(p-phenylenebenzobisoxazole) fiber (Zylon: registered trademark), or the like may be used as the fiber of the cover material 22.

FIG. 5 depicts the heat resistance temperatures and the Young's moduli of these fibers together with the heat resistance temperatures and the Young's moduli of the optical fiber and polyimide. Note that, in FIG. 5, the temperature at the melting point of the optical fiber is given as the heat resistance temperature thereof, while the softening point temperatures or the decomposition temperatures of the polyimide coating, the PBO fiber, the PAN-based carbon fiber, and the high-silica glass fiber are given as the heat resistance temperatures thereof.

As depicted in FIG. 5, the heat resistance temperature of the optical fiber (core and cladding) is about 1000° C., and the heat resistance temperature of the polyimide coating is about 300° C. to 400° C.

The high-silica glass fiber, the PAN-based carbon fiber, and the PBO fiber all have better heat resistance than polyimide which is the coating material. However, the Young's modules of each of these fibers are the same or higher than the Young's modules of the optical fibers. Accordingly, simply bundling yarns made of these fibers around the primary-coated optical fiber 21 in parallel causes the tensile force applied to the primary-coated optical fiber 21 to decrease in the application of the tensile force, and it is not possible to detect an abnormality.

Meanwhile, in the embodiment, the cover material 22 obtained by braiding yarns of the glass fiber, the PAN fiber, or the PBO fiber is used, and the primary-coated optical fiber 21 is disposed inside the cover material 22. Accordingly, the cover material 22 is stretchable in the longitudinal direction of the primary-coated optical fiber 21 although the Young's modulus of the fiber is high.

In the optical fiber cord 20 according to the embodiment, the cover material 22 easily stretches when bending stress or tensile stress is applied to the optical fiber cord 20, and the stress is transmitted to the primary-coated optical fiber 21. The stress may be thus detected by the primary-coated optical fiber 21.

Moreover, in the optical fiber cord 20 according to the embodiment, the fiber with a higher heat resistance temperature than that of the coating material 21b is used for the cover material 22. Accordingly, the optical fiber cord 20 may be used in a high temperature environment for a long time.

Furthermore, in the optical fiber cord 20 according to the embodiment, since the primary-coated optical fiber 21 is disposed inside the cover material 22, the primary-coated optical fiber 21 is less likely to be damaged and a certain level of mechanical strength is also secured.

In FIGS. 4A and 4B, the primary-coated optical fiber 21 is disposed inside the cover material 22. However, a reinforcement core yarn may be inserted in the cover material 22 together with the primary-coated optical fiber 21 to prevent breakage of the primary-coated optical fiber 21 in manufacturing. The reinforcement core yarn may be braided with the yarns made of the fiber in the cover material 22. Moreover, a secondary-coated optical fiber may be used instead of the primary-coated optical fiber 21.

In the case of actually using the optical fiber cord 20 illustrated in FIGS. 4A and 4B, each of end portions of the cover material 22 is preferably subjected to termination to prevent the yarns made of the fiber from fraying.

Figure 6A:
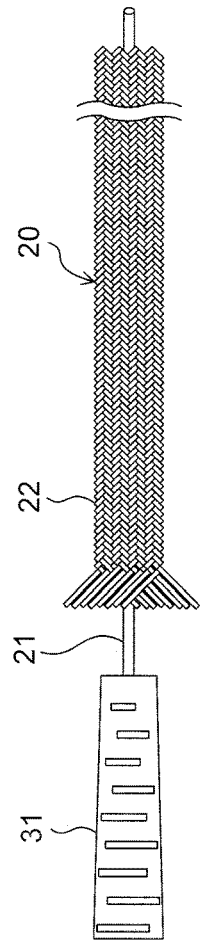
FIGS. 6A to 6C are views illustrating an example of a termination method for a cover material.
Figure 6B:
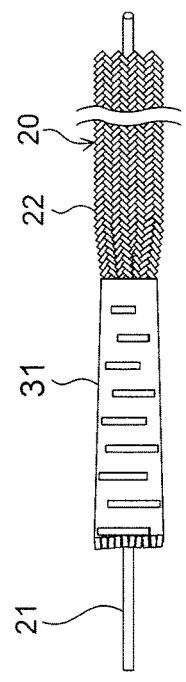
Figure 6C:
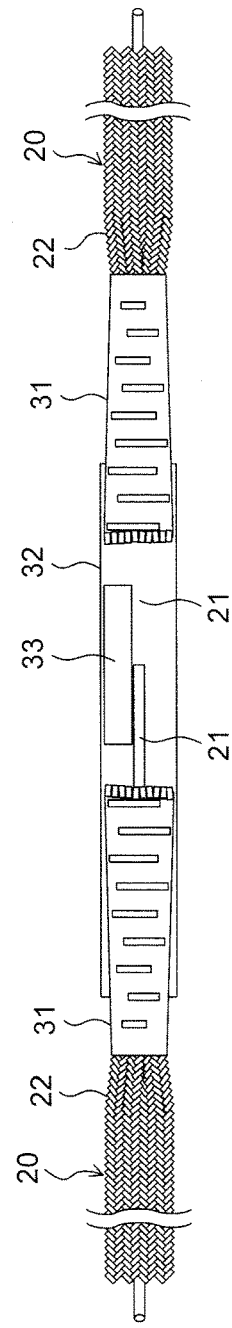

FIGS. 6A to 6C are views illustrating an example of a termination method of the cover material 22. In the following description, each of the yarns forming the cover material 22 is referred to as side yarn. In the embodiment, a multifilament obtained by twisting together a plurality of monofilaments into one yarn is used as the side yarn.

First, as illustrated in FIG. 6A, a tubular resin boot 31 is prepared and an end portion of the optical fiber cord 20 is inserted into the boot 31. Then, as illustrated in FIG. 68, the boot 31 is disposed at the end portion of the cover material 22, and the end portion (side yarns) of the cover material 22 is folded at a periphery of the boot 31 to be cut along an end portion of the boot 31.

Next, as illustrated in FIG. 6C, two optical fiber cords 20 to which the boots 31 are attached are disposed such that ends of the two optical fiber cords 20 face each other. Then, a heat shrinking tube 32 is fitted to a periphery of one of the optical fiber cords 20. Thereafter, an end of the optical fiber 21a in the one optical fiber cord 20 and an end of the optical fiber 21a in the other optical fiber cord 20 are fused to be optically connected to each other.

Next, a reinforcement metal rod 33 is disposed along the fused portion of the optical fibers 21a. Then, the heat shrinking tube 32 is moved to the connection portion and is caused to shrink by being heated. The termination of the optical fiber cords 20 may be thus performed, and fraying of the side yarns of the cover material 22 is avoided.

FIGS. 7A to 7E are views illustrating another example of the termination method of the cover material 22.

Figure 7A:
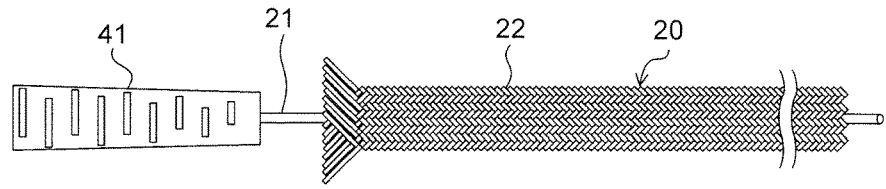
FIGS. 7A to 7E are views illustrating another example of the termination method for the cover material.
Figure 7B:
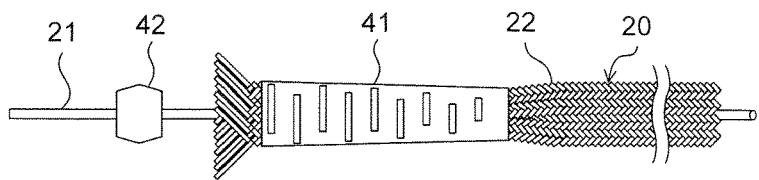

First, as illustrated in FIG. 7A, a cylindrical resin boot 41 is prepared, and the end portion of the optical fiber cord 20 is inserted into the boot 41. Next, as illustrated in FIG. 7B, the boot 41 is disposed at the end portion of the cover material 22, and the end portion (side yarns) of the cover material 22 are folded at a periphery of the boot 41 to be cut along an end portion of the boot 41.

Then, an end of the primary-coated optical fiber 21 is passed through an annular metal fitting 42, and the metal fitting 42 is partially inserted into the cover material 22.

Figure 7C:
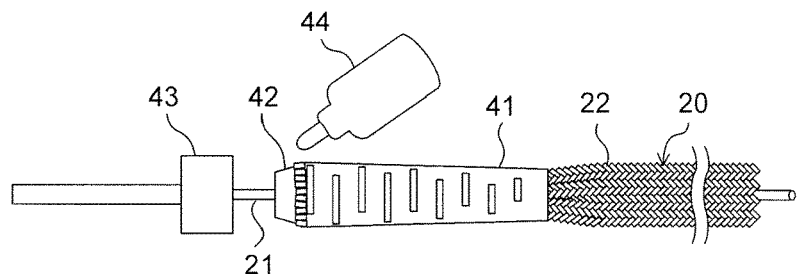

Next, as illustrated in FIG. 7C, the end portion of the primary-coated optical fiber 21 is inserted into a ferrule 43 with a flange which is made of zirconia. Then, the ferrule 43 and the metal fitting 42 are bonded to each other by adhesive 44.

Figure 7D:
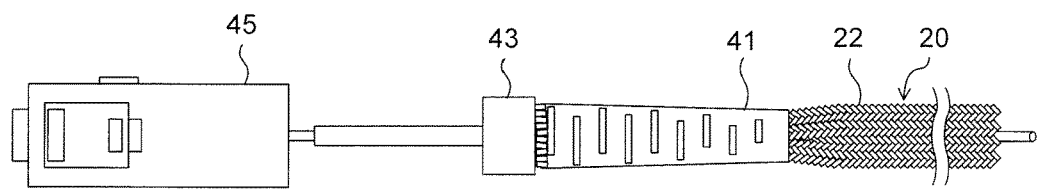
Figure 7E:
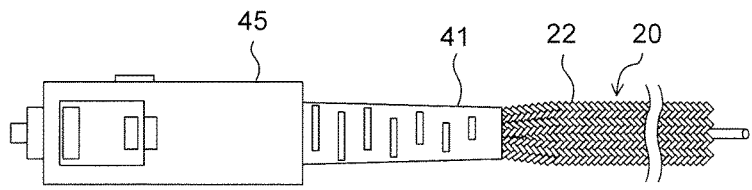

Next, as illustrated in FIG. 7D, the end portion of the optical fiber cord 20 is inserted into a SC connector 45, and the SC connector 45 is fixed at such a position that an end portion of the ferrule 43 slightly protrudes from the SC connector 45 as illustrated in FIG. 7E. Thereafter, the end portion of the primary-coated optical fiber 21 is polished such that an end surface of the ferrule 43 and an end surface of the optical fiber 21a are aligned with each other.

The termination of the optical fiber cord 20 is thus completed, and fraying of side yarns of the cover material 22 is avoided.

A method of manufacturing the optical fiber cord 20 according to the embodiment is described below.

Figure 8:
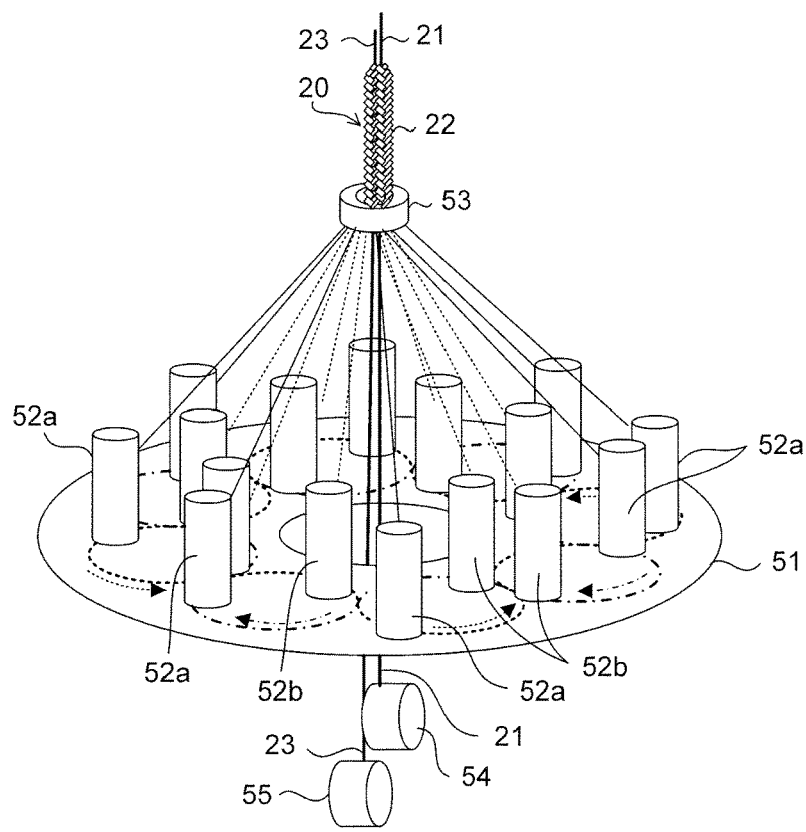
FIG. 8 is a schematic view illustrating an example of a braiding machine.

FIG. 8 is a schematic view illustrating an example of a braiding machine. The braiding machine includes an annular turn table 51 which is horizontally arranged. A plurality of bobbins 52a and 52b around which yarns (multifilament) to be the side yarns of the cover material 22 are wound are arranged on the turn table 51.

The bobbins 52a are each moved counterclockwise on the turn table 51 by a drive mechanism (not illustrated) disposed below the turn table 51 with the distance of the bobbin 52a from the center of the turn table 51 periodically varying. Moreover, the bobbins 52b are each moved clockwise on the turn table 51 by the drive mechanism disposed below the turn table 51 with the distance of the bobbin 52b from the center of the turn table 51 periodically varying. The trajectories of the bobbins 52a (illustrated by broken lines in FIG. 8) and the trajectories of the bobbins 52b (illustrated by one-dot chain lines in FIG. 8) periodically intersect one another.

The yarns unwounded from the bobbins 52a and 52b pass through an inside of an annular braiding opening 53 disposed above the turn table 51, and are braided into the cover material 22.

A bobbin 54 around which the primary-coated optical fiber 21 is wound and a bobbin 55 around which a reinforcement core yarn 23 is wound are disposed below the turn table 51. The primary-coated optical fiber 21 and the reinforcement core yarn 23 unwounded from the bobbins 54 and 55 pass through a center portion of the turn table 51, are introduced into to the braiding opening 53, and are disposed inside the cover material 22. The cover material 22 in which the primary-coated optical fiber 21 and the core yarn 23 are inserted is taken up by a take-up roll (not illustrated). The optical fiber cord 20 according to the embodiment is thus manufactured.

Figure 9:
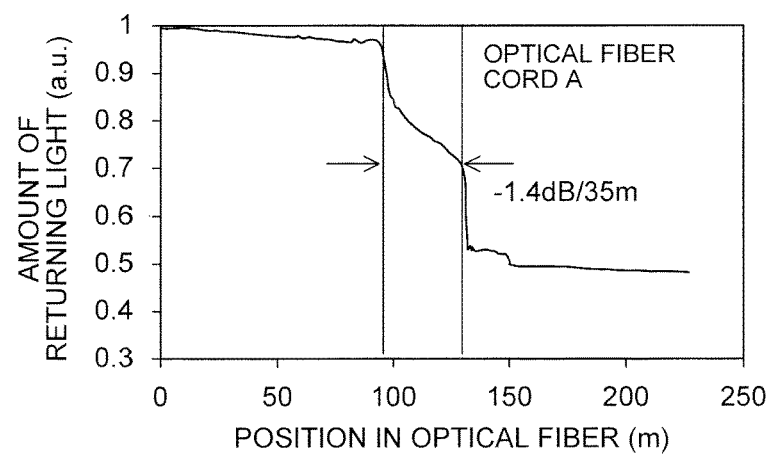
FIG. 9 is a graph depicting a result of examining transmission loss in an optical fiber cord A (trial product)

An optical fiber cord manufactured in the aforementioned method as a trial product (hereafter, referred to as "optical fiber cord A") is connected to a distributed temperature sensor (DTS) to examine the transmission loss thereof. The transmission loss is −1.4 db/35 m as depicted in FIG. 9 and is great. In the optical fiber cord A, Zylon with a count (thickness) of 1110 g/10 km is used for the side yarns and the reinforcement core yarn. Moreover, the cover material is formed by braiding 16 side yarns. Note that, in this example, the optical fiber cord A is formed such that part of the primary-coated optical fiber is covered with the cover material.

A situation where the primary-coated optical fiber is continuously bent in a radius smaller than the minimum allowable bending radius due to constriction by the side yarns and the core yarn is considered as a possible reason for the transmission loss of the optical fiber cord A being great. In view of this, an X-ray photograph of the optical fiber cord A is taken. However, it is found from the X-ray photograph that the primary-coated optical fiber is bent in a sufficiently large bending radius in the cover material, and there is no bending smaller than the minimum allowable bending radius.

Moreover, a situation where, in the optical fiber cord A, the optical fiber is scratched by Zylon in the course of manufacturing and abrasion is formed in the optical fiber is considered as a possible reason for the increase of the transmission loss.

In view of this, optical fiber cords in which a high-silica glass multifilament as hard as the optical fiber is used for the side yarns are manufactured as trial products. The count of the high-silica glass multifilament used for the side yarns is 450 g/km. An optical fiber cord formed by braiding four side yarns (hereafter, referred to as "optical fiber cord B") and an optical fiber cord formed by braiding eight side yarns (hereafter, referred to as "optical fiber cord C") are manufactured. Note that, also in this example, the optical fiber cords B and C are each formed such that part of the primary-coated optical fiber is covered with the cover material.

Figure 10:
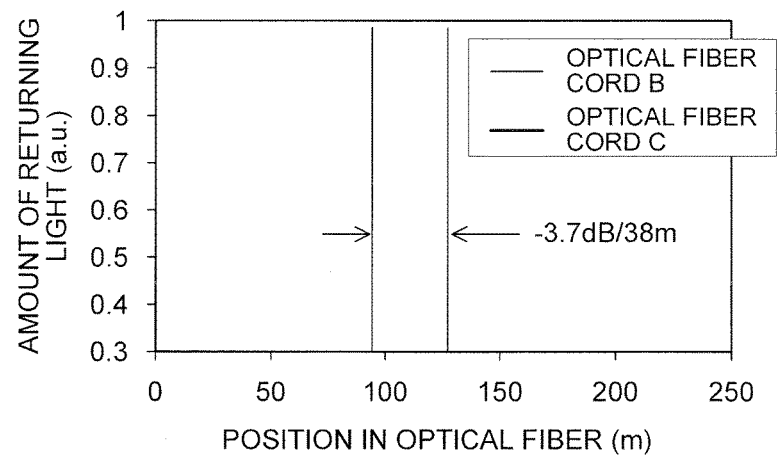
FIG. 10 is a graph depicting results of examining transmission loss in optical fiber cords B and C (trial products)

The optical fiber cords B and C are connected to the distributed temperature sensor (DTS) to examine the transmission loss thereof. The transmission loss is about −3.7 db/38 m as depicted in FIG. 10 in both cords.

Figure 11:
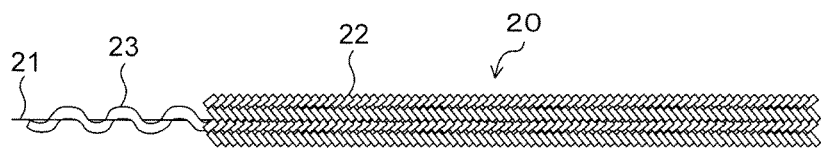
FIG. 11 is a schematic view illustrating a state where a core yarn is twined around a primary-coated optical fiber.

The primary-coated optical fibers are taken out from the optical fiber cords A, B, and C, and there is no external damage in all of the primary-coated optical fibers. However, as schematically illustrated in FIG. 11, the core yarn 23 is twined around the primary-coated optical fiber 21. It is inferred from this that the transmission loss is great in the optical fiber cords A, B, and C because torsional stress is applied to the primary-coated optical fiber 21.

The structure of the braiding machine used to manufacture the optical fiber cords A, B, and C is left-right symmetric. Accordingly, when the number of side yarns braided clockwise and the number of side yarns braided counterclockwise are the same, it is expected that clockwise torsional stress and counterclockwise torsional stress are balanced, and the core yarn 23 is not twined around the primary-coated optical fiber 21.

However, it is conceived that either one of the clockwise torsional stress or the counterclockwise torsional stress actually becomes greater than the other due to a filament tolerance, a difference in amounts of filaments remaining in bobbins, an error in a position of the braiding opening, and the like, and stress acts in such a direction that the primary-coated optical fiber is twisted. This may explain why the core yarn 23 is periodically twined around the primary-coated optical fiber 21 as in FIG. 11.

For example, decreasing the contact area between the primary-coated optical fiber and the side yarns by increasing the number of side yarns and increasing a gap between the primary-coated optical fiber and the side yarns (cover material) is conceivable as measures for reducing the torsional stress acting on the primary-coated optical fiber.

For example, when the high-silica glass fiber with a count of 450 g/km is used for the side yarns, the thickness of one side yarn is about 0.3 mm to 0.9 mm. When 24 or more side yarns made of this high-silica glass fiber are used, the outer diameter of the cover material is about 6.6 mm and a gap of 2 mm or more in average is secured between the primary-coated optical fiber and the cover material.

In the case of manufacturing such an optical fiber cord, a gap between the primary-coated optical fiber and the side yarns may be secured at the position of the braiding opening. However, in the taking up of the optical fiber cord by the take-up roll, the primary-coated optical fiber comes into contact with the side yarns and torsional stress is generated in the primary-coated optical fiber.

Moreover, in the case of using such an optical fiber cord as a temperature sensor, the optical fiber cord has a problem that responsiveness to temperature change is poor due to a large gap between the cover material and the primary-coated optical fiber.

In the embodiment, the problems described above are overcome by adjusting a braiding pitch.

Figure 12:
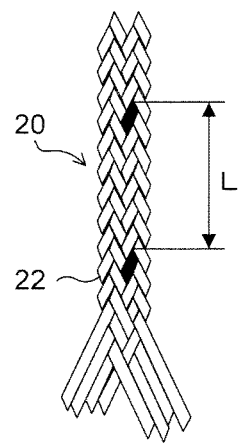
FIG. 12 is a schematic view for explaining a braiding pitch.

As schematically illustrated in FIG. 12, a braiding pitch L is defined as an average value of the distance which the side yarn proceeds while going around the optical fiber cord 20 once in a state where no external force is applied to the cover material 22.

The braiding pitch L may be adjusted by, for example, changing the distance between the turn table 51 and the braiding opening 53 in FIG. 8. Increasing the distance between the turn table 51 and the braiding opening 53 reduces an entrance angle of each yarn at the braiding opening 53 (angle between the yarn and the vertical axis), and the braiding pitch L is thereby increased. Meanwhile, reducing the distance between the turn table 51 and the braiding opening 53 increases the entrance angle of each yarn at the braiding opening 53, and the braiding pitch L is thereby reduced.

Incidentally, the reason why the transmission loss of the optical fiber increases when the torsional stress acts on the optical fiber is because the torsional stress causes a tensile strain in the optical fiber.

Figure 13:
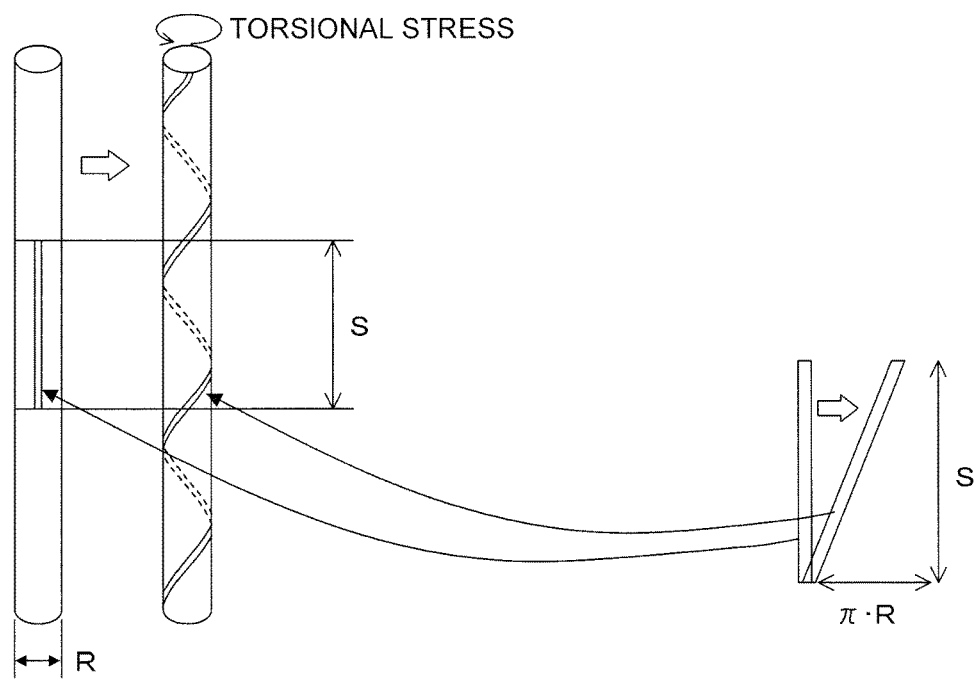
FIG. 13 is a view illustrating a relationship between a twist pitch and a tensile strain of the optical fiber.

FIG. 13 is a view illustrating a relationship between a twist pitch and the tensile strain of the optical fiber. The tensile strain W (%) is expressed by the following formula (1), where R represents the diameter of the optical fiber, and S represents the twist pitch of the optical fiber.

[Math 1]

$$W(\%) = (\sqrt{S^2 + (\pi \cdot R)^2} - S) + S \qquad (1)$$

Figure 14:
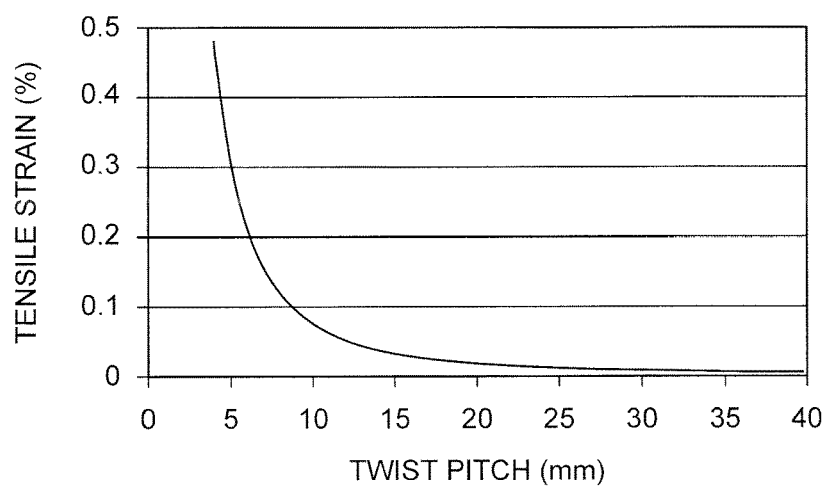
FIG. 14 is a graph depicting a relationship between the twist pitch and the tensile strain.

FIG. 14 is a graph depicting a relationship between the twist pitch S and the tensile strain W (%), where the horizontal axis represents the twist pitch S and the vertical axis represents the tensile strain W (%). In this example, the diameter of the optical fiber is 0.125 mm. It is found from FIG. 14 that the tensile strain W increases as the twist pitch S becomes shorter.

It is generally said that the tensile strain of the optical fiber being 0.2% or less is preferable from the view point of the life of the optical fiber, and this value is used as a guide in the manufacturing of the optical fiber.

It is found from the formula (1) that the tensile strain of the optical fiber with the diameter of 0.125 mm may be set to 0.2% or less by setting the twist pitch S to 6.2 mm or more.

Figures 15, 16:
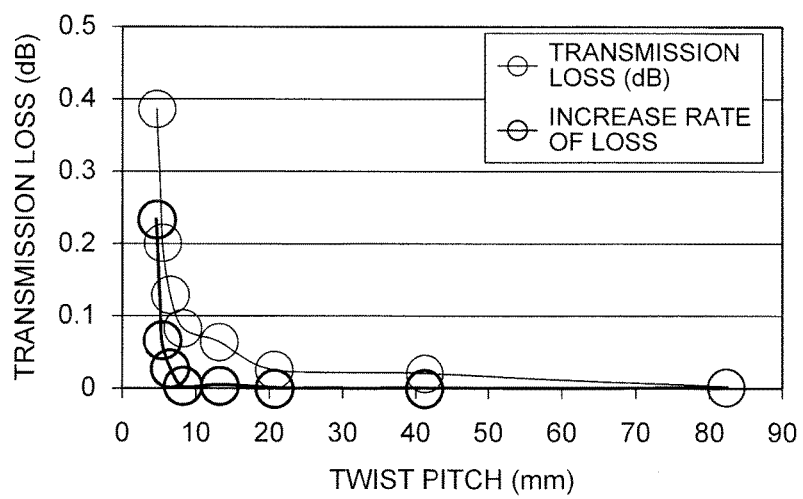
FIG. 15 is a graph depicting results of examining a relationship between the twist pitch and the transmission loss and a relationship between the twist pitch and an increase rate of the transmission loss, which is performed by actually twisting the optical fiber.
FIG. 16 depicts materials, thickness (counts), numbers, and braiding pitches of yarns used as side yarns of the cover material, and results of examining elongation of the cover materials formed of these yarns.

FIG. 15 is a graph depicting results of examining a relationship between the twist pitch and the transmission loss and a relationship between the twist pitch and an increase rate of the transmission loss, which is performed by actually twisting the optical fiber. In this case, the optical fiber is fixed at two positions away from each other by 70 cm in the longitudinal direction of the optical fiber, and the transmission loss is measured while the optical fiber between the two positions is twisted.

It is found from FIG. 15 that the transmission loss sharply increases when the twist pitch is between 8.25 mm to 5.5 mm. Moreover, it is found from FIG. 14 that the tensile strain in the case where the twist pitch is 8.25 mm to 5.5 mm is 0.11% to 0.25%.

From these results, it is found that the transmission loss is sufficiently small at a twist pitch at which the tensile strain is 0.2% or less.

Since the twisting of the optical fiber occurs due to fiction with the side yarns in the braiding, the twist pitch S does not exceed the braiding pitch L. This means that the transmission loss may be sufficiently reduced by setting the braiding pitch L of the cover material to S or less, S being the twist pitch at which the tensile strain is 0.2% or less.

For example, when the diameter of the optical fiber is 0.125 mm, the twist pitch S at which the tensile strain is 0.2% is 6.2 mm. Accordingly, an optical fiber cord with sufficiently small transmission loss may be obtained by setting the braiding pitch L to 6.2 mm or more. Incidentally, the braiding pitches of the optical fiber cords B and C illustrated in FIG. 10 are measured, and the braiding pitch of the optical fiber cord B is 5 mm while the braiding pitch of the optical fiber cord C is 5.5 mm.

FIG. 16 depicts results of examining elongation of cover materials of optical fiber cords in the case where load of 200 gram-weight is applied to the cover materials, the optical fiber cords being manufactured to have the structure illustrated in FIGS. 4A and 4B, where yarns used as the side yarns vary in material, thickness (count), the number of yarns used, and braiding pitch among the cover materials.

Note that, in this example, a primary-coated optical fiber obtained by applying carbon coating or polyimide coating to an optical fiber with a diameter of 0.125 mm is used. The diameter of the primary-coated optical fiber is 0.15 mm.

As depicted in FIG. 16, the braiding pitch L of each of the manufactured optical fiber cords No. 1 to No. 5 is 6.2 mm or more. Moreover, while the elongation of the primary-coated optical fiber in the case where load of 200 gram-weight is applied thereto is 1.05 mm, the elongation of each of the cover materials is 1.6 mm or more and is greater than the elongation of the primary-coated optical fiber.

In other words, the optical fiber cords No. 1 to No. 5 may be used in an abnormality detection system configured to detect changes in stress by detecting changes in transmission loss.

Figure 17:
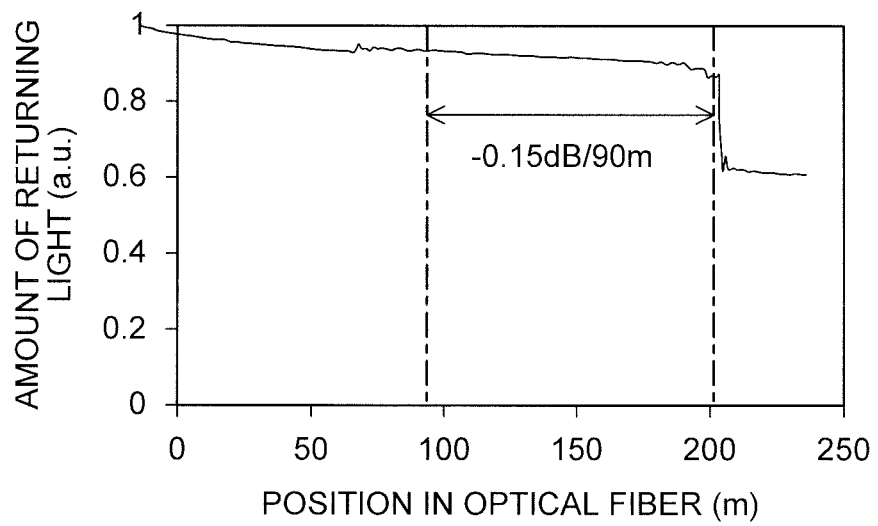
FIG. 17 is a graph depicting a result of measuring the transmission loss of the optical fiber cord No. 3.

FIG. 17 is a graph depicting a result of measuring the transmission loss of the optical fiber cord No. 3 which is connected to the distributed temperature sensor (DTS). As depicted in FIG. 17, the transmission loss of the optical fiber cord No. 3 in a section of 90 m is 0.15 db. When this value is converted into the transmission loss in 1 km, the value is 1.66 dB and is substantially the same value as the transmission loss of the primary-coated optical fiber alone.

Figure 18:
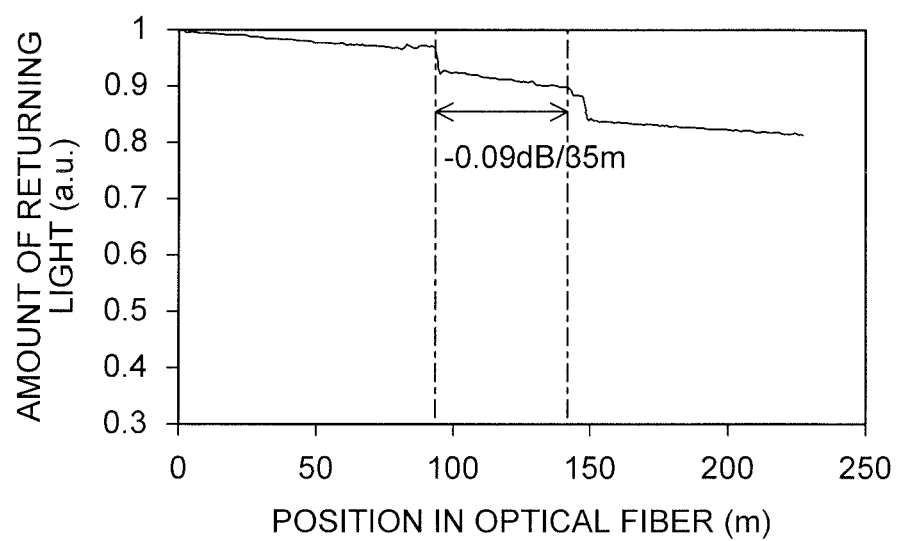
FIG. 18 is a graph depicting a result of measuring the transmission loss of the optical fiber cord No. 5.

FIG. 18 is a graph depicting a result of measuring the transmission loss of the optical fiber cord No. 5 which is connected to the distributed temperature sensor (DTS). As depicted in FIG. 18, the transmission loss of the optical fiber cord No. 5 in a section of 35 m is 0.09 db. When this value is converted into the transmission loss in 1 km, the value is 2.57 dB. This value is greater than the transmission loss of the optical fiber cord No. 3, but the degree of this value is all right for practical use.

Figure 19:
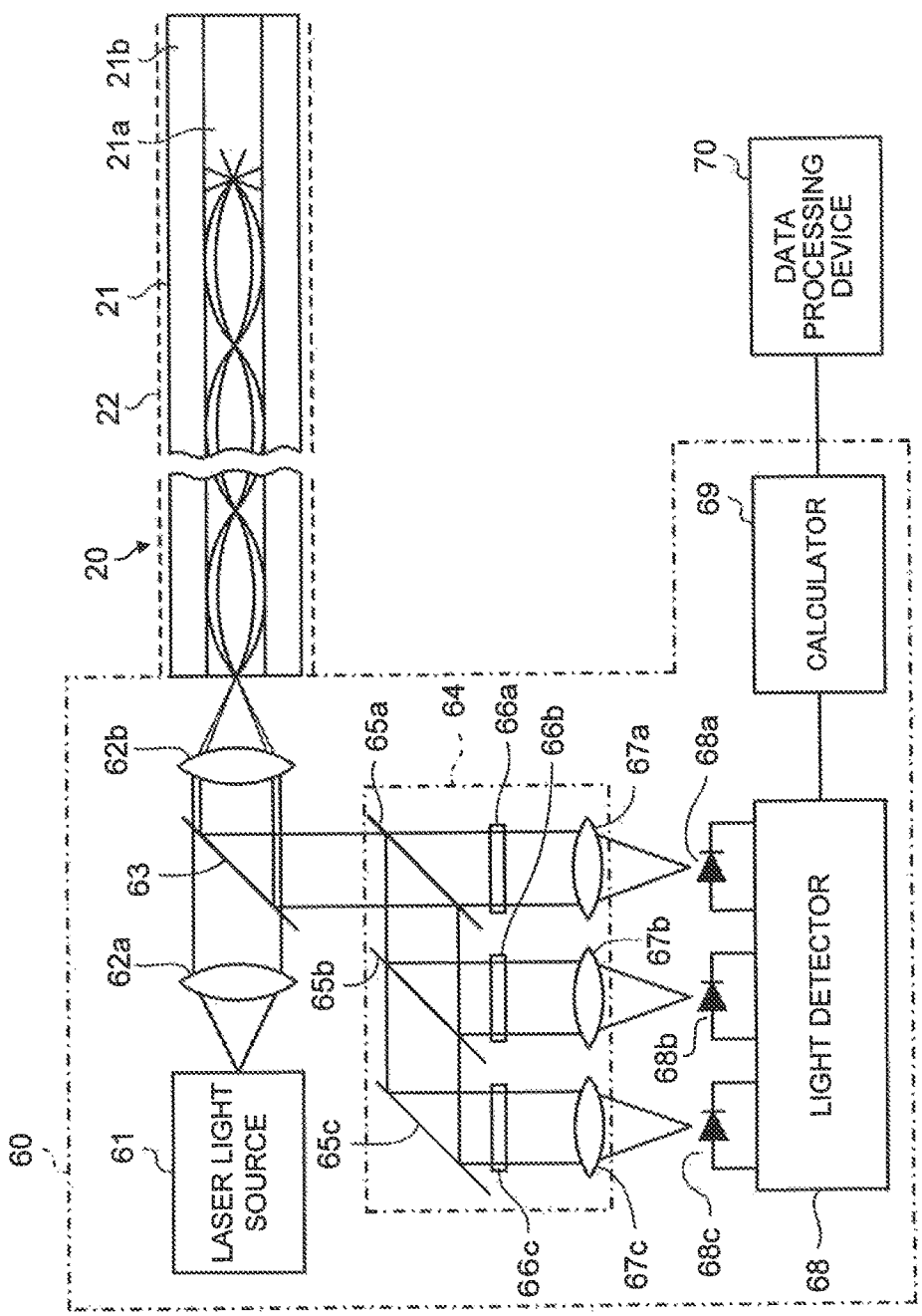
FIG. 19 is a block diagram illustrating an abnormality detection system according to the embodiment.
Figure 20:
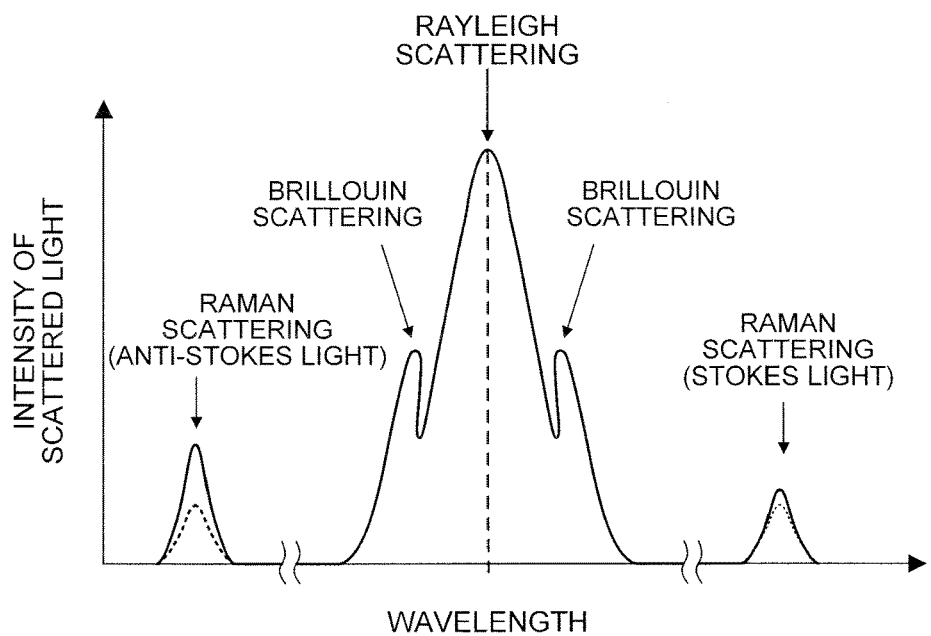
FIG. 20 is a graph depicting a spectrum of backscattered light.
Figure 21:
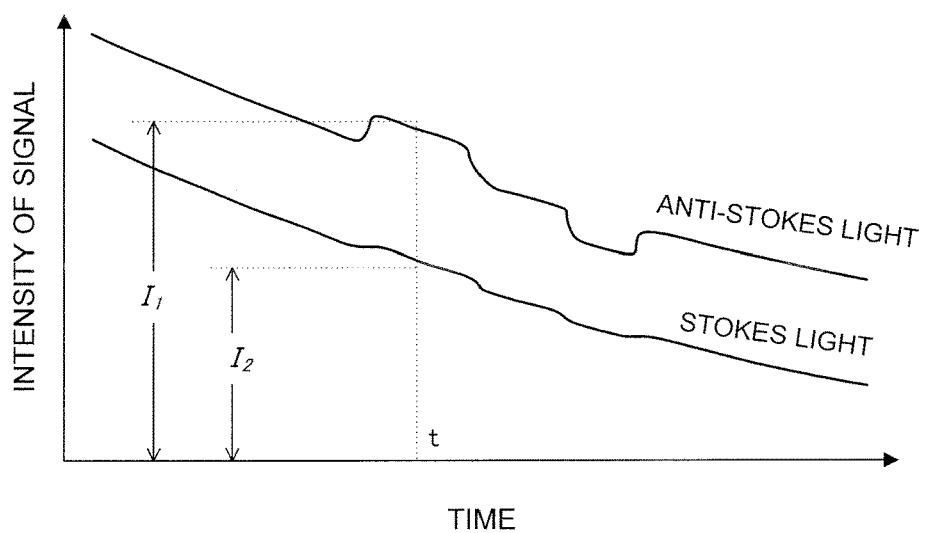
FIG. 21 is a graph depicting time series distribution of intensity of Raman scattered light detected by a scattered light detector.

(Abnormality Detection System) FIG. 19 is a block diagram illustrating the abnormality detection system according to the embodiment. Moreover, FIG. 20 is a graph depicting a spectrum of backscattered light, and FIG. 21 is a graph depicting time series distribution of intensity of Raman scattered light detected by a scattered light detection device.

As illustrated FIG. 19, the abnormality detection system according to the embodiment includes the optical fiber cord 20, the scattered light detection device 60, and a data processing device 70 configured to process data outputted from the scattered light detection device 60. The scattered light detection device 60 is an example of a scattered light detector, and the data processing device 70 is an example of a data processor.

As illustrated FIG. 19, the scattered light detection device 60 includes a laser light source 61, lenses 62a and 62b, a beam splitter 63, a wavelength separator 64, a light detector 68, and a calculator 69, and is used by being connected to the optical fiber cord 20.

The optical fiber cord 20 includes the primary-coated optical fiber 21 and the braided cover material 22 as illustrated in FIGS. 4A and 4B. Moreover, the primary-coated optical fiber 21 includes the optical fiber 21a and the coating material 21b covering the peripheral surface of the optical fiber 21a. The diameter R of the primary-coated optical fiber 21 is 0.150 mm, and the braiding pitch L of the cover material 22 is 6.2 mm or more. The diameter R of the primary-coated optical fiber 21 and the braiding pitch L of the cover material 22 satisfy the relationship of the following formula (2). [Math 2]

$$(\sqrt{L^2 + (\pi \cdot R)^2} - L) + L \leq 0.2(\%) \qquad (2)$$

For example, the optical fiber cord 20 is laid around the pipes 11 and 12 as illustrated in FIG. 1, and is partially fixed to the pipes 11 and 12 by the tapes 14 and the like.

Laser light of a predetermined pulse width is emitted from the laser light source 61 at a fixed cycle. The laser light passes through the lens 62a, the beam splitter 63, and the lens 62b and enters the optical fiber 21a from a light source side end portion of the optical fiber 21a.

Part of the light entering the optical fiber 21a is backscattered by molecules forming the optical fiber 21a. As depicted in FIG. 20, the backscattered light includes a Rayleigh scattered light, a Brillouin scattered light, and a Raman scattered light. The Rayleigh scattered light is light having the same wavelength as the incident light, while the Brillouin scattered light and the Raman scattered light are lights having wavelengths shifted from the wavelength of the incident light.

The Raman scattered light includes a Stokes light whose wavelength shifts to become longer than that of the incident light and an anti-Stokes light whose wavelength shifts to become shorter than that of the incident light. The intensities of the Stokes light and the anti-Stokes light change depending on the temperature. The change amount of the Stokes light depending on the temperature is small, while the change amount of the anti-Stokes light depending on the temperature is great. In other words, it may be said that the temperature dependency of the Stokes light is small, and the temperature dependency of the anti-Stokes light is great.

As illustrated in FIG. 19, these backscattered lights go back the optical fiber 21a and are outputted from the light source side end portion of the optical fiber 21a. Then, the lights pass through the lens 62b, are reflected by the beam splitter 63, and enter the wavelength separator 64.

The wavelength separator 64 includes beam splitters 65a to 65c which transmit or reflect lights depending on their wavelengths and optical filters 66a to 66c which each transmit a light of a certain wavelength. The wavelength separator 64 also includes focusing lenses 67a to 67c which focus lights having passed through the optical filters 66a to 66c respectively on light receiving portions 68a to 68c of the light detector 68.

The light having entered the wavelength separator 64 is separated into the Rayleigh scattered light, the Stokes light, and the anti-Stokes light by the beam splitters 65a to 65c and the optical filters 66a to 66c, and the lights are inputted into the light receiving portions 68a to 68c of the light detector 68. As a result, signals corresponding to the intensities of the Rayleigh scattered light, the Stokes light, and the anti-Stokes light are outputted from the light receiving portions 68a to 68c.

The calculator 69 includes a computer. The calculator 69 stores changes of the signals outputted from the light detector 68 over time, and calculates the ratio between intensities of the Stokes light and the anti-Stokes light to obtain the temperature distribution in the longitudinal direction of the optical fiber 21a.

The back scattered light generated in the optical fiber 21a attenuates while going back the optical fiber 21a. Accordingly, it is important to take in consideration of the attenuation of the light to correctly evaluate the temperate at a position where the backscattering has occurred.

FIG. 21 is a graph depicting an example of the time series distribution of the intensity of the Raman scattered light, where the horizontal axis represents time and the vertical axis represents signal intensity. The light detector 68 detects the Stokes light and the anti-Stokes light for a certain period from a time point just after the entrance of the laser pulse into the optical fiber 21a. When the temperature is uniform over the entire length of the optical fiber 21a, the signal intensity decreases with the elapse of time, relative to the signal intensity at the time point of the entrance of the laser pulse into the optical fiber 21a. In this case, the time in the horizontal axis indicates the distance from the light source side end portion of the optical fiber 21a to the position where the backscattering has occurred, and the decrease of the signal intensity over time indicates the attenuation of the light due to the optical fiber 21a.

When the temperature is not uniform over the entire optical fiber 21a in its longitudinal direction, for example, when a high temperature portion and a low temperature portion exist in the longitudinal direction, the signal intensities of the Stokes light and the anti-Stokes light do not attenuate uniformly, and peaks and valleys appear in curves indicating the changes of the signal intensities over time as depicted in FIG. 21. In FIG. 21, the intensity of the anti-Stokes light at a certain time t is denoted by $I_1$, while the intensity of the Stokes light at the certain time t is denoted by $I_2$.

Figure 22:
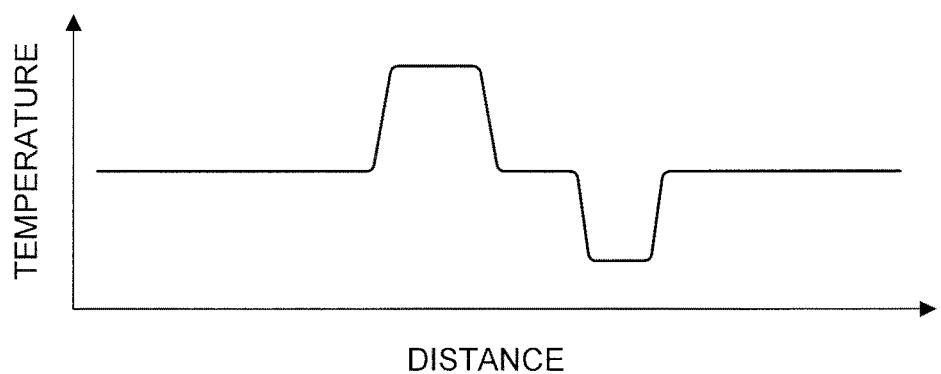
FIG. 22 is a graph which depicts a result of calculating an $I_1/I_2$ ratio based on the time series distribution of the intensity of the Raman scattered light in FIG. 21 and in which the horizontal axis (time) and the vertical axis (signal intensity) of FIG. 21 are converted respectively to distance and temperature.

FIG. 22 is a graph which depicts a result of calculating an $I_1/I_2$ ratio based on the time series distribution of the intensity of the Raman scattered light in FIG. 21 and in which the horizontal axis (time) and the vertical axis (signal intensity) of FIG. 21 are converted respectively to distance and temperature. As depicted in FIG. 22, the temperature distribution in the longitudinal direction of the optical fiber may be measured by calculating the ratio ($I_1/I_2$) between the intensities of the anti-Stokes light and the Stokes light.

The scattered light detection device 60 used in the embodiment has a structure which is basically the same as that of the distributed temperature sensor (DTS), and may measure the temperature distribution as described above. However, the measurement of the temperature distribution may be performed as needed, and is not essential.

Data of the temperature distribution in the longitudinal direction of the optical fiber like the one described above and data of the intensity distribution of the returning light (Stokes light, anti-Stokes light, and Rayleigh scattered light) in the longitudinal direction of the optical fiber like the one illustrated in FIG. 2 are outputted from the scattered light detection device 60.

The data processing device 70 includes a computer. The data processing device 70 processes the data outputted from the scattered light detection device 60 and determines whether an abnormality is present. When determining that an abnormality is present, the data processing device 70 executes preset processing such as giving a warning.

Storing a route along which the optical fiber cord is laid (optical fiber cord laid route in a two-dimensional or three-dimensional space) in the data processing device 70 enables calculation of a temperature distribution in the two-dimensional or three-dimensional space, from the temperature distribution in the longitudinal direction of the optical fiber 21a which is outputted from the scattered light detection device 60. Since characters, numbers, and the like may be printed on the cover material 22 of the optical fiber cord 20, it is possible to, for example, print the distance from a reference point on the cover material of the optical fiber cord and thereby facilitate processing of creating data of the optical fiber cord laid route.

The inventors of this application have proposed a temperature measurement method in which temperature measurement values at various measurement points are corrected by using a transfer function, with the temperature at a certain measurement point being used as a reference (International Publication Pamphlet No. WO 2010/125712 and the like). In this method, the temperatures at the measurement points set along the longitudinal direction of the optical fiber at intervals of ten to several tens of centimeters may be accurately detected.

By the way, the stress applied to the optical fiber may be detected from the intensity distribution of the returning light in the longitudinal direction of the optical fiber like the one illustrated in FIG. 2. Applying a differential FIR (Finite Impulse Response) filter on the intensity distribution of the returning light reduces a noise content and emphasizes the transmission loss.

Figure 23:
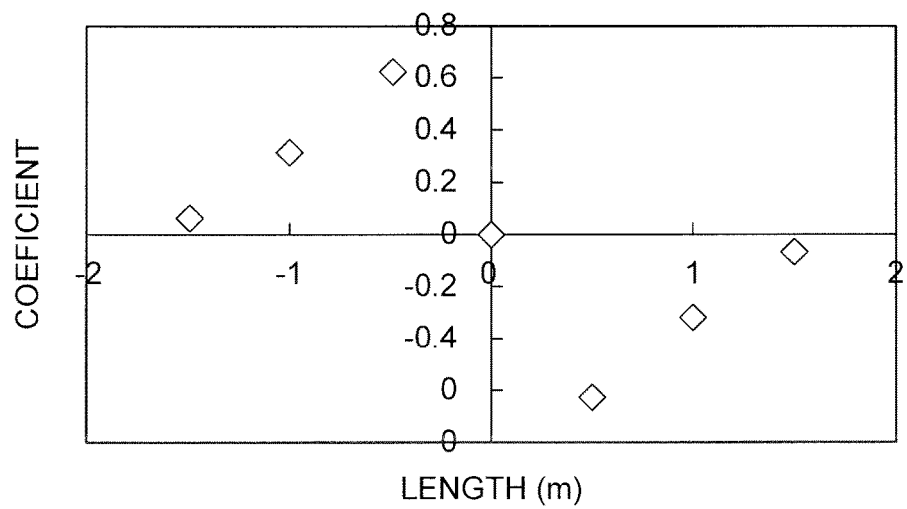
FIG. 23 is a view illustrating an example of a FIR filter.

The differential FIR filter is a filter which has the characteristics of a differential filter and a low-pass filter, unlike a unit step type differential filter. An example of the FIR filter used in the embodiment is illustrated in FIG. 23. The transmission loss may be emphasized by, for example, calculating products of results obtained by applying the FIR filter to the intensity distributions of the Stokes light and the anti-Stokes light for each of positions in the longitudinal direction of the optical fiber, and then calculating a root of a sum of squares of the calculated products for each of positions in the longitudinal direction of the optical fiber.

Alternatively, the transmission loss may be emphasized by calculating a product of: a result of applying the FIR filter to the intensity distribution of the Stokes light which is obtained when the laser light is made to enter the optical fiber from one end portion of the optical fiber; and a result of applying the FIR filter to the intensity distribution of the Stokes light which is obtained when the laser light is made to enter the optical fiber from the other end portion of the optical fiber, for each of positions in the longitudinal direction of the optical fiber.

As another alternative, the transmission loss may be emphasized by obtaining the intensity distribution of the Stokes light which is obtained when the laser light is made to enter the optical fiber from one end portion of the optical fiber and the intensity distribution of the Stokes light which is obtained when the laser light is made to enter the optical fiber from the other end portion of the optical fiber, creating a function of these Stokes lights by using a normalization function, and applying the FIR filter.

Figure 24A:
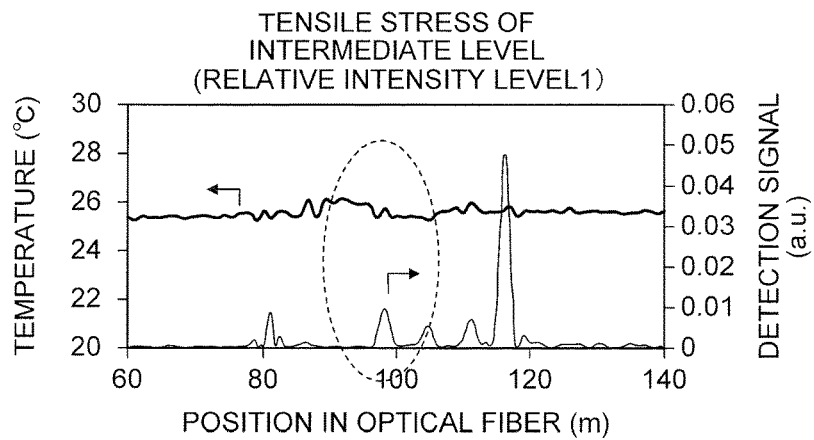
FIGS. 24A to 24C are graphs depicting measurement results of temperature distribution and measurement results (after application of the FIR filter) of a stress detection signal in the cases where tensile stress of an intermediate level (relative intensity level 1), slightly stronger tensile stress (relative intensity level 2), and strong tensile stress (relative intensity level 2.8) are applied to the optical fiber cord No. 4 in FIG. 16.
Figure 24B:
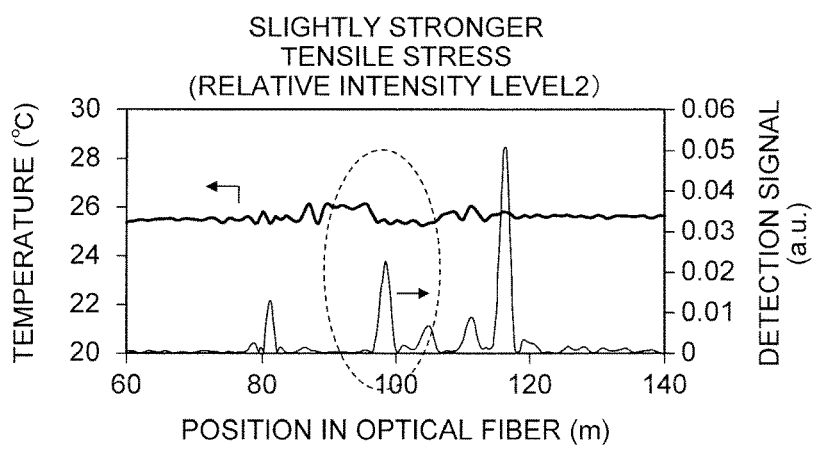
Figure 24C:
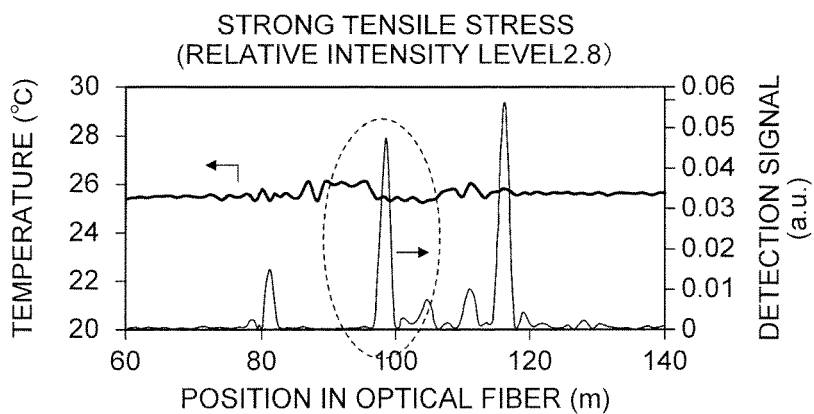

FIG. 24A is a graph depicting a measurement result of temperature distribution and a measurement result (after application of the FIR filter) of a stress detection signal in the case where tensile stress of an intermediate level (relative intensity level 1) is applied to the optical fiber cord No. 4 in FIG. 16. Moreover, FIG. 24B is a graph depicting a measurement result of the temperature distribution and a measurement result (after application of the FIR filter) of the stress detection signal in the case where slightly stronger tensile stress (relative intensity level 2) is applied to the same optical fiber cord. Furthermore, FIG. 24C is a graph depicting a measurement result of the temperature distribution and a measurement result (after application of the FIR filter) of the stress detection signal in the case where strong tensile stress (relative intensity level 2.8) is applied to the same optical fiber cord. The tensile stress is applied to the optical fiber cord at a position which is about 97 m away from the reference point of the optical fiber.

It is found from FIGS. 24A to 24C that the signals corresponding to the applied tensile stress may be detected. Moreover, it is found that the temperature distribution is substantially the same irrespective of the level of the tensile stress, and the tensile stress does not affect the measurement of the temperature distribution.

Note that a large peak appearing near a point of 118 m in each of FIGS. 24A to 24C is formed due to transmission loss in a connector portion.

Figure 25:
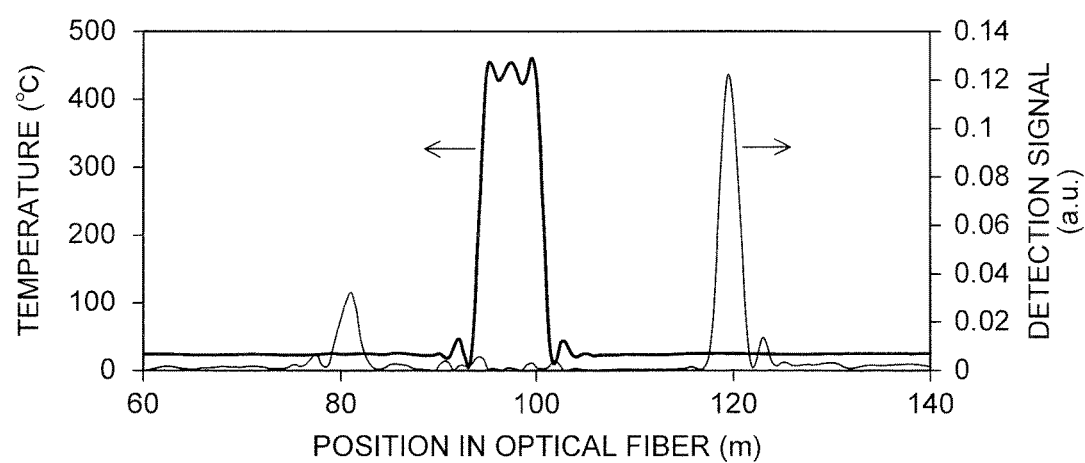
FIG. 25 is a graph depicting results obtained when transmission loss measurement and temperature distribution measurement are performed simultaneously by using the optical fiber cord No. 4.

FIG. 25 is a graph depicting results obtained when transmission loss measurement and temperature distribution measurement are performed simultaneously by using the optical fiber cord No. 4 in FIG. 16. In this case, part of the optical fiber cord (section of about 8 m) is placed inside an electric furnace while being wound into a loop having a diameter of about 8 cm, and is heated to a temperature of about 450° C. Also in this case, it is possible to simultaneously perform the temperature distribution measurement and the abnormality detection by means of detecting changes in stress.

As described above, the abnormality detection system according to the embodiment uses the optical fiber cord 20 as a sensor, the optical fiber cord 20 including the cover material formed by braiding yarns made of the fiber having the heat resistance temperature of 300° C. or more. The abnormality detection system may thus simultaneously perform the temperature distribution measurement and the abnormality detection by means of detecting changes in stress, in an environment where the temperature is 300° C. or more.

All examples and conditional language recited herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An optical fiber cord comprising: an optical fiber; and a cover material covering the optical fiber, the cover material being formed by braiding a plurality of yarns with a same yarn count, the plurality of yarns being braided to physically intersect one another in the cover material, wherein an adherentless gap is provided between the optical fiber and the cover material, and the cover material is not adhered to the optical fiber.

2. The optical fiber cord according to claim 1, wherein $$(((L^2+(\pi \cdot R)^2))^{1/2}-L) \div L \leq 0.2(\%)$$

is satisfied, where R is a diameter of the optical fiber and L is a braiding pitch of the cover material.

3. The optical fiber cord according to claim 1, wherein a peripheral surface of the optical fiber is coated with a coating material made of carbon or resin.

4. The optical fiber cord according to claim 3, wherein a Young's modulus of the yarns forming the cover material is greater than a Young's modulus of the coating material.

5. The optical fiber cord according to claim 3, wherein a heat resistance temperature of the cover material is higher than a heat resistance temperature of the coating material.

6. The optical fiber cord according to claim 1, wherein elongation of the cover material alone is greater than elongation of the optical fiber alone when a same load is applied to the cover material and the optical fiber.

7. The optical fiber cord according to claim 1, wherein data indicating a distance from a reference point is printed on the cover material.

8. The optical fiber cord according to claim 1, further comprising:

a core yarn inserted between the optical fiber and the cover material.

9. An abnormality detection system comprising: an optical fiber covered with a cover material formed by braiding a plurality of yarns with a same yarn count, the plurality of yarns being braided to physically intersect one another in the cover material; a scattered light detector configured to detect scattered light occurring in the optical fiber and output data on intensity distribution of the scattered light in a longitudinal direction of the optical fiber; and a data processor configured to determine presence or absence of an abnormality based on the data outputted from the scattered light detector, wherein an adherentless gap is provided between the optical fiber and the cover material, and the cover material is not adhered to the optical fiber.

10. The abnormality detection system according to claim 9, wherein $$(((L^2+(\pi \cdot R)^2))^{1/2}-L) \div L \leq 0.2 (\%)$$

is satisfied, where R is a diameter of the optical fiber and L is a braiding pitch of the cover material.

11. The abnormality detection system according to claim 9, wherein a peripheral surface of the optical fiber is coated with a coating material made of carbon or resin.

12. The abnormality detection system according to claim 11, wherein a Young's modulus of the yarns forming the cover material is greater than a Young's modulus of the coating material.

13. The abnormality detection system according to claim 11, wherein a heat resistance temperature of the cover material is higher than a heat resistance temperature of the coating material.

14. The abnormality detection system according to claim 9, wherein elongation of the cover material alone is greater than elongation of the optical fiber alone when a same load is applied to the cover material and the optical fiber.

15. The abnormality detection system according to claim 9, wherein the scattered light detector further detects temperature distribution in a longitudinal direction of the optical fiber from a detection result of the scattered light occurring in the optical fiber.

16. The abnormality detection system according to claim 9, wherein the data processor applies a FIR (Finite Impulse Response) filter to the data outputted from the scattered light detector or a function receiving the data outputted from the scattered light detector as an input.

17. The abnormality detection system according to claim 9, wherein the optical fiber is laid along a pipe.

18. The abnormality detection system according to claim 9, further comprising:

a core yarn inserted between the optical fiber and the cover material.

* * * * *